(12) United States Patent
Krattiger

(10) Patent No.: US 8,167,470 B2
(45) Date of Patent: May 1, 2012

(54) ILLUMINATION DEVICE FOR GENERATING LIGHT AND SUPPLYING THE LIGHT TO AN OBSERVATION DEVICE USED IN ENDOSCOPY OR MICROSCOPY

(75) Inventor: Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 607 days.

(21) Appl. No.: 12/337,056

(22) Filed: Dec. 17, 2008

(65) Prior Publication Data

US 2009/0154192 A1    Jun. 18, 2009

(30) Foreign Application Priority Data

Dec. 17, 2007 (DE) .......................... 10 2007 063 262

(51) Int. Cl.
*G02B 6/00* (2006.01)
(52) U.S. Cl. .......................... 362/574; 362/294; 362/556
(58) Field of Classification Search .................. 362/572, 362/574, 580, 231, 554, 555, 556; 385/116, 385/117
See application file for complete search history.

(56) References Cited

U.S. PATENT DOCUMENTS

| | | | |
|---|---|---|---|
| 4,773,723 A | 9/1988 | Cuda | |
| 5,289,555 A | 2/1994 | Sanso | |
| 5,847,759 A | 12/1998 | Williams et al. | |
| 6,692,431 B2 | 2/2004 | Kazakevich | |
| 6,880,954 B2 * | 4/2005 | Ollett et al. | 362/245 |
| 2003/0147254 A1 | 8/2003 | Yoneda et al. | |
| 2004/0246744 A1 | 12/2004 | Krupa et al. | |
| 2005/0140270 A1 | 6/2005 | Henson et al. | |
| 2006/0171693 A1 | 8/2006 | Todd et al. | |

FOREIGN PATENT DOCUMENTS

| | | |
|---|---|---|
| WO | 9808123 A1 | 2/1998 |
| WO | 01/75359 A1 | 10/2001 |

OTHER PUBLICATIONS

European Search Report; EP 08 17 1287; Apr. 8, 2009; 3 pages.

* cited by examiner

*Primary Examiner* — John A Ward
(74) *Attorney, Agent, or Firm* — St. Onge Steward Johnston & Reens LLC

(57) ABSTRACT

An illumination device for generating light and supplying the light to an observation device used in endoscopy or microscopy comprises a light source having at least one LED and at least one optical waveguide to guide the light emitted by the light source. The proximal end of the optical waveguide is arranged on a side of the light source which faces the optical waveguide. The illumination device furthermore comprises a cooling device to dissipate heat generated by the light source, which cooling device has at least one first cooling element for dissipating the heat generated by the light source, which cooling element is arranged on a side of the light source which faces away from the proximal end of the optical waveguide. The cooling device has a second cooling element for dissipating the heat generated by the light source, which second cooling element is arranged on the side of the light source which faces the proximal end of the optical waveguide. The at least one optical waveguide passes through the second cooling element.

20 Claims, 11 Drawing Sheets

ILLUMINATION DEVICE FOR GENERATING LIGHT AND SUPPLYING THE LIGHT TO AN OBSERVATION DEVICE USED IN ENDOSCOPY OR MICROSCOPY

CROSS-REFERENCE TO RELATED APPLICATIONS

The present application claims priority of German patent application No. 10 2007 063 262.4 filed on Dec. 17, 2007.

FIELD OF THE INVENTION

The invention generally relates to illumination devices for use in endoscopy or microscopy. More specifically, the invention relates to an illumination device for generating light and supplying light into an observation device used in endoscopy or microscopy, wherein the illumination device comprises a light source having at least one LED.

BACKGROUND OF THE INVENTION

By way of example, an illumination device is used in endoscopy or microscopy to illuminate a region to be observed. The illumination device can be attached to an endoscope or microscope by means of a light conducting cable, or it can be directly connected to the observation device. The light is guided within the illumination device by means of, for example, light conducting optics in the form of optical elements and/or optical waveguides. So as to ensure an optimum illumination of the region to be observed, the illumination device must provide sufficient luminous power. However, due to the high luminous power, the illumination device generates large amounts of heat which has to be dissipated so that the performance of the illumination device is not impaired.

An illumination device known from U.S. Pat. No. 6,692,431 B2 can be plugged onto a proximal end of the head of an endoscope and has a plurality of LEDs as light sources which are arranged on ribs of a metal body of the illumination device, which ribs run in the axial direction. Proximal ends of optical waveguides are arranged directly on the light emitting surfaces of the LEDs and the optical waveguides are combined to form optical waveguide bundles. The optical waveguide bundles are combined to form a fibre optic loom in the region of the distal end of the illumination device, which loom is connected to the light conducting optics of the endoscope via a light coupling-in element.

A disadvantage of the known illumination device is that the heat generated by the LEDs can only be dissipated via the axial ribs of the metal body arranged on the side of the LEDs which faces away from the proximal ends of the optical waveguides of the optical waveguide bundles. However, since the LEDs also emit heat via their light emitting surfaces, the proximal ends of the optical waveguides, which are arranged directly on the surface of the LED, heat up. This can disadvantageously impair the functionality of the optical waveguides so that the maximum luminous power of the optical waveguides is limited by the insufficient heat dissipation.

Moreover, it is disadvantageous that all light emitting surfaces of the LEDs are connected to optical waveguides for the purposes of providing light generated by the LEDs as illumination light for the endoscope. In particular, those surface regions of the LEDs which emit little light are also contacted by optical waveguides in the process; as a result of this, the maximum light intensity of the optical waveguide bundles in the case of a predetermined optical waveguide bundle cross section is reduced due to the arrangement of optical waveguides in the regions with a low light emission.

SUMMARY OF THE INVENTION

Hence, it is an object of the invention to provide a remedy in this case and to improve an illumination device of the type mentioned initially to the effect that an efficient cooling of the illumination device and at the same time an increase in the light intensity are made possible.

According to an aspect of the invention, an illumination device for generating light and supplying the light to an observation device used in endoscopy or microscopy is provided, comprising a light source having at least one LED, at least one optical waveguide having a proximal end and a distal end, the proximal end being arranged on a side of the light source which faces the optical waveguide. A cooling device to dissipate heat generated by the light source is provided, wherein the cooling device has at least one first cooling element for dissipating heat generated by the light source, the at least one first cooling element being arranged on a side of the light source which faces away from the proximal end of the optical waveguide. The cooling device has a second cooling element for dissipating heat generated by the light source, the second cooling element being arranged on a sight of the light source which faces the proximal end of the optical waveguide, the at least one optical waveguide passing through the second cooling element.

The illumination device according to the invention has a first cooling element on a side of the light source which faces away from the proximal end of the optical waveguide, so that the heat generated by the light source can be dissipated to the rear of the light source. The illumination device furthermore has an additional second cooling element on the side of the light source which faces the proximal end of the optical waveguide through which the proximal end of the optical waveguide passes. As a result of this, the heat emitted by the light emitting surface of the LED is absorbed by the second cooling element and dissipated. Furthermore, the optical waveguide, loaded with the heat generated by the light source, is also cooled since it transmits the heat absorbed by its outer surface to the second cooling element. The cooling concept according to the invention therefore is particularly efficient; as a result of this, the light source and the optical waveguide are advantageously sufficiently cooled and the illumination device maintains its functionality despite heating up.

Preferably, the cooling device has a cooling body which is connected to the first and/or the second cooling element in a thermally conducting fashion.

In this case, a thermally conducting connection of two components is understood to be a direct or indirect thermal contact; as a result of this, heat exchange between the two components, in particular dissipation of heat from the warmer component to the cooler component, is made possible.

Due to the presence of the cooling body designed, for example, to be solid and to be made from a material with a high thermal conductivity, the illumination device is advantageously cooled in an improved manner since the cooling body absorbs the heat of the cooling elements heated by the light source, and emits it to the surroundings via its surface. The cooling body can be designed as a passive cooler, for example in the form of a heat pipe or a sufficiently large metal block. An additional, thermally conducting connection of the cooling body to a housing wall of the illumination device furthermore prevents an accumulation of heat within the illumination device, since the heat absorbed by the cooling body can be efficiently dissipated to the surroundings.

In a preferred refinement of the invention, additional optical waveguides pass through the second cooling element, with the optical waveguides being arranged at a distance from one another in the region of the second cooling element.

Increasing the number of optical waveguides in the illumination device advantageously leads to an increase in the maximum light intensity supplied, since a greater luminous energy can be transmitted to the observation device. Due to the fact that the at least one optical waveguide and/or the additional optical waveguides passes or pass through the second cooling element, the proximal ends of the optical waveguides heated by the light source are furthermore sufficiently cooled; as a result of this, the light-guiding capability of the optical waveguides is not disadvantageously impaired. The arrangement at a distance of the proximal ends of the optical waveguides in the second cooling element effects an increase in the outer surface of the optical waveguides which can be used for heat dissipation compared to a thick optical waveguide; as a result of this, the entire second cooling element is advantageously used for heat dissipation of the heat emitted by the optical waveguides, and the illumination device is cooled in a further improved manner.

The optical waveguides are preferably connected to form a fibre optic loom on the distal side of the second cooling element; as result of this it is possible to guide the optical waveguides in a particularly simple and space-saving fashion from the second cooling element to a distal end of the illumination device. The optical waveguides can be connected, for example, by adhesively connecting the outer surfaces of the individual optical waveguides.

In a further preferred refinement of the invention, the at least one optical waveguide and/or the additional optical waveguides is or are arranged in regions of the light source with a high light emission intensity.

It is often the case that the light emission intensity of an LED surface is not constant across the extent of the LED surface, so that the light emitting LED surface comprises regions with a high light emission intensity and regions with a low or average light emission intensity. The regions with a low or average light emission intensity can be caused, for example, by the arrangement of electrical supply structures (lines or the like), which at least partly absorb the light generated by the light source. As a result of using regions with a high light emission intensity to provide the light intensity for the illumination device, the light intensity provided for illuminating the region to be observed per optical waveguide cross section is on average higher than an arrangement of optical waveguides over the entire LED surface, and hence optimal luminous efficiency is achieved.

In an alternative preferred refinement of the invention, the at least one optical waveguide and/or the additional optical waveguides is or are arranged in regions of the light source with a high light emission intensity and in regions of the light source with a low light emission intensity, with the optical waveguides arranged in the regions with a high light emission intensity being able to be connected to the proximal end of the light conducting cable.

In this refinement of the illumination device, the optical waveguides are arranged distributed across the entire LED surface, so that all the light emitted by the LED is used, regardless of the light emission intensity of the individual regions. Selecting those optical waveguides arranged in regions with a high light emission for transporting light to the observation device also provides on average a higher maximum light intensity of the illumination device than when using all optical waveguides to provide the light intensity. The optical waveguides arranged in the regions with a low or average light emission can be used, for example, for effect lighting of the front panel or for displaying the operational state of the illumination device. The advantage of this measure is that all the light emitted by the LED is used effectively. In addition, the optical waveguides can automatically be arranged on the LED, since the optical waveguides to be arranged can, for example, be affixed to the LED surface in a regularly distributed fashion.

In a further preferred refinement of the invention, the at least one optical waveguide and/or the additional optical waveguides are designed as optical fibres, liquid optical waveguides and/or solid light conducting elements.

The specified refinements of the optical waveguides can also be implemented in a combined form in the illumination device. An optical waveguide is conventionally designed as a transparent body, on the inner faces of which the light is repeatedly diverted by total internal reflection due to a jump in the refractive index or a refractive index gradient and/or due to reflection at a metallic reflective layer, and hence the light is transmitted. In the case of a refinement of the optical waveguide or the optical waveguides as optical fibres made of, for example, glass or plastics, the optical waveguides are preferably combined in the region of their proximal ends to form optical waveguide bundles which pass through the second cooling element. In connection with a refinement of the optical waveguide and/or the optical waveguides as liquid optical waveguides, the optical waveguides can be designed as flexible cables of a suitable diameter which are filled with a liquid and pass through the second cooling element. It is also possible that, in the region of the second cooling element, the optical waveguide or optical waveguides are designed as liquid optical waveguides such that the passages of the second cooling element, through which the optical waveguides pass, are used as inlet or outlet lines for a liquid which can circulate along a surface of the light source. As a result of this, provision is made for liquid cooling of the light source which contributes to a further improved cooling of the illumination device. In the case of a refinement of the optical waveguides as solid light conducting elements, the optical waveguides are preferably designed as glass rods, rods of diamond or sapphire, or else as plastic rods.

In a further preferred refinement of the invention, the second cooling element comprises, at least along part of its side which faces the light source, a heat diffusion element for dissipating the heat generated by the light source into the second cooling element.

The effect of this measure is that the heat generated by the light source is transferred into the second cooling element in a further improved fashion by the arrangement of the additional heat diffusion element; as a result of this, the heat transport of the heat generated by the light source away from the latter is advantageously assisted, so that a further improved cooling of the illumination device is achieved. The heat diffusion element is preferably designed as a transparent plate which extends at least in part along a surface of the heat diffusion element which faces the light source, so that the light emitted by the light source can pass through it and can be coupled into the proximal ends of the optical waveguides. Furthermore, the heat diffusion element is preferably designed to be sufficiently thin so that the light intensity provided by the illumination device is not disadvantageously impaired by absorption in the heat diffusion element. The heat diffusion element can likewise have cut-outs in the region of the optical waveguides, through which the optical waveguides can pass. Furthermore, extending the heat diffusion element along preferably the entire surface of the second cooling element which faces the light source affords the possibility of optimal heat dissipation of the heat generated by the light source into the second cooling element.

In a further preferred refinement of the invention, at least one optical waveguide of the optical waveguides has a heat absorption element which dissipates the heat of the one optical waveguide and which is inserted into the one optical waveguide on the proximal side.

The effect of this measure is that the heat absorption element, inserted into the optical waveguide on the proximal side, can directly absorb the heat generated by the light source; as a result of this, the optical waveguide is heated less compared to a refinement of the second cooling element without an additional heat absorption element. The heat absorption element is designed, for example, as a plate-shaped insert of diamond, for example.

In connection with the refinement of the illumination device having the heat diffusion element, the heat diffusion element and the heat absorption element are preferably arranged directly adjacent to one another so that the end faces which face one another of the two components abut; as a result of this, a particularly compact design of the second cooling element can advantageously be achieved.

In a further preferred refinement of the invention, the at least one optical waveguide and/or the additional optical waveguides running through the second cooling element have an approximately quadrilateral cross-section.

The effect of this measure is that the surrounding heat conductor networks have a comparatively high thermal conduction value compared to a hexagonal shape, so the dissipation of heat is advantageously particularly high. Furthermore, the production of the cooling element is particularly simple since quadrilateral passages for the optical waveguides can be made particularly easily in the second cooling element. It is understood that quadrilateral cross sections of the optical waveguide bundles can for example also comprise optical waveguide cross sections which are in the form of rectangles, squares or parallelograms.

In a further preferred refinement of the invention, the first cooling element and the second cooling element are connected in a thermally conducting fashion.

This measure effects heat interchange between the two cooling elements so that the heat can advantageously be transferred from the warmer cooling element to the cooler cooling element. In the case of the refinement of the illumination device with the additional cooling body which is preferably connected in a thermally conducting fashion to at least one of the two cooling elements, the heat generated by the light source is dissipated in a further improved manner; as a result of this, the functionality of the illumination device is not disadvantageously impaired by the heating of its components.

In a further preferred refinement of the invention, the proximal end of the optical waveguide and/or the proximal ends of the optical waveguides are arranged directly on the light source.

The effect of this measure is that the light emitted by the light source is directly coupled into the optical waveguides without light coupling-in elements in the form of, for example, a lens or a fibre cone; as a result of this, there advantageously is no loss of light intensity at the light coupling-in site and an optimum effective cross section for the light coupling into the proximal ends of the optical waveguides is achieved. Furthermore, the direct arrangement of the optical waveguides on the light source affords the possibility of only that light which is emitted by the corresponding light source sections being coupled into the proximal ends of the optical waveguides. In connection with arranging the optical waveguides in regions with a high light emission intensity, this thus prevents light from regions with a low or average light emission intensity also being coupled into the proximal ends of the optical waveguides; as a result of this, a maximum light intensity per optical waveguide cross section is achieved. The direct arrangement of the optical waveguide ends on the light source furthermore affords the possibility of a particularly compact and, at the same time, very simple construction of the illumination device since, for example, additional spacers for the proximal ends of the optical waveguides are avoided. The direct arrangement of the optical waveguides on the light source can be effected by, for example, pressing the proximal ends of the optical waveguides onto the surface of the LED or by adhesively connecting the appropriate components.

In an alternative preferred refinement of the invention, the proximal end of the optical waveguide and/or the proximal ends of the optical waveguides are arranged at a short distance from the light source.

The advantage of this measure is that, as in the case of directly arranging the optical waveguides on the light source, there are no additional light coupling-in elements present between the light source and the proximal ends of the optical waveguides; as a result of this, a particularly small light coupling-in angle can be achieved and advantageously there is no light intensity loss at the light coupling-in site. Furthermore, the reduction of the light intensity in the optical waveguides by coupling-in light emitted by regions with a low or average light emission intensity is prevented.

In connection with the direct arrangement of the optical waveguides on the light source, or an arrangement at a short distance therefrom, it is understood that, depending on the desired effect, the optical waveguides of the illumination device can partly be arranged directly on the light source and partly arranged at a short distance from the light source.

In a further preferred refinement of the invention, an optical contact means is arranged between the proximal end of the optical waveguide and the light source and/or between the proximal ends of the optical waveguides and the light source.

This measure effects refractive index matching between the material of the light source and the material of the optical waveguide so that advantageously reflection losses in the light intensity at the light coupling-in site between the light source and the optical waveguides are reduced. By way of example, the optical contact means can be a transparent adhesive, a transparent refractive-index gel or a transparent (cooling) liquid.

In a further preferred refinement of the invention, the light source has, at least in part, a light modulation layer on the side which faces the proximal end of the optical waveguide for modulating a property of the light emitted by the light source, preferably for modulating a wavelength of the light emitted by the light source.

The effect of this measure is that different properties of the light generated by the light source can be set in a targeted manner, depending on the desired light property, with regard to polarization, wavelength, intensity, etc. In particular, the illumination device can provide different wavelengths for illuminating the region to be observed so that the illumination device according to the invention can advantageously be used in a number of different ways. By way of example, the light modulation layer can be designed as a phosphorous layer so that a white light results in the case of an LED emitting blue light.

In a further preferred refinement of the invention, the light modulation layer is arranged in regions with a high light emission intensity.

The advantage of this measure is that the production of the illumination device is particularly cost-effective because the light modulation layer is only arranged on those regions of the light source on which the proximal ends of an optical waveguide are arranged.

In a further preferred refinement of the invention, the light modulation layer is thermally conducting or at least provided with a thermally conducting coating.

This measure effects additional heat dissipation of heat generated by the light source into the second cooling element; as a result of this, the cooling of the illumination device is advantageously further improved.

In a further preferred refinement of the invention, a distal end of the at least one optical waveguide and/or distal ends of the additional optical waveguides have an antireflection coating.

The effect of this measure is that no light, which is led along the optical waveguide to the proximal end of the light conducting cable from the light source, is reflected back to the light source. It is for this reason that the illumination device advantageously has an even higher luminous power since there is no light intensity loss at the coupling-in site into the observation device.

In a further preferred refinement of the invention, the distal ends of the optical waveguides are fused together and/or fused with the light modulation layer.

This method effects a reduction in the cross section of the optical waveguides in the region of the coupling-in site into the light conducting cable so that advantageously the cross section of the optical waveguide and the light conducting cable can be matched. This is particularly advantageous in connection with arranging the optical waveguides in the regions with a high and low light emission from the light source, since in this refinement a particularly large number of optical waveguides are guided from the light source to the light cable. Additionally, the reflection loss is reduced in the case of fusion with the light modulation layer.

In a further preferred refinement of the invention, the light source comprises a plurality of LEDs.

The advantage of this measure is that standard LED chips, which have a plurality of LEDs in the form of an array, can be used.

Further advantages and features emerge from the following description and the attached drawing.

It is understood that the features mentioned above and the features which are still to be explained below can be used not only in the specified combinations, but also in other combinations or on their own without departing from the scope of the present invention.

BRIEF DESCRIPTION OF THE DRAWINGS

The invention is explained and described in more detail below on the basis of a few selected exemplary embodiments in connection with the attached drawings, in which.

DETAILED DESCRIPTION OF THE INVENTION

Figure 1:
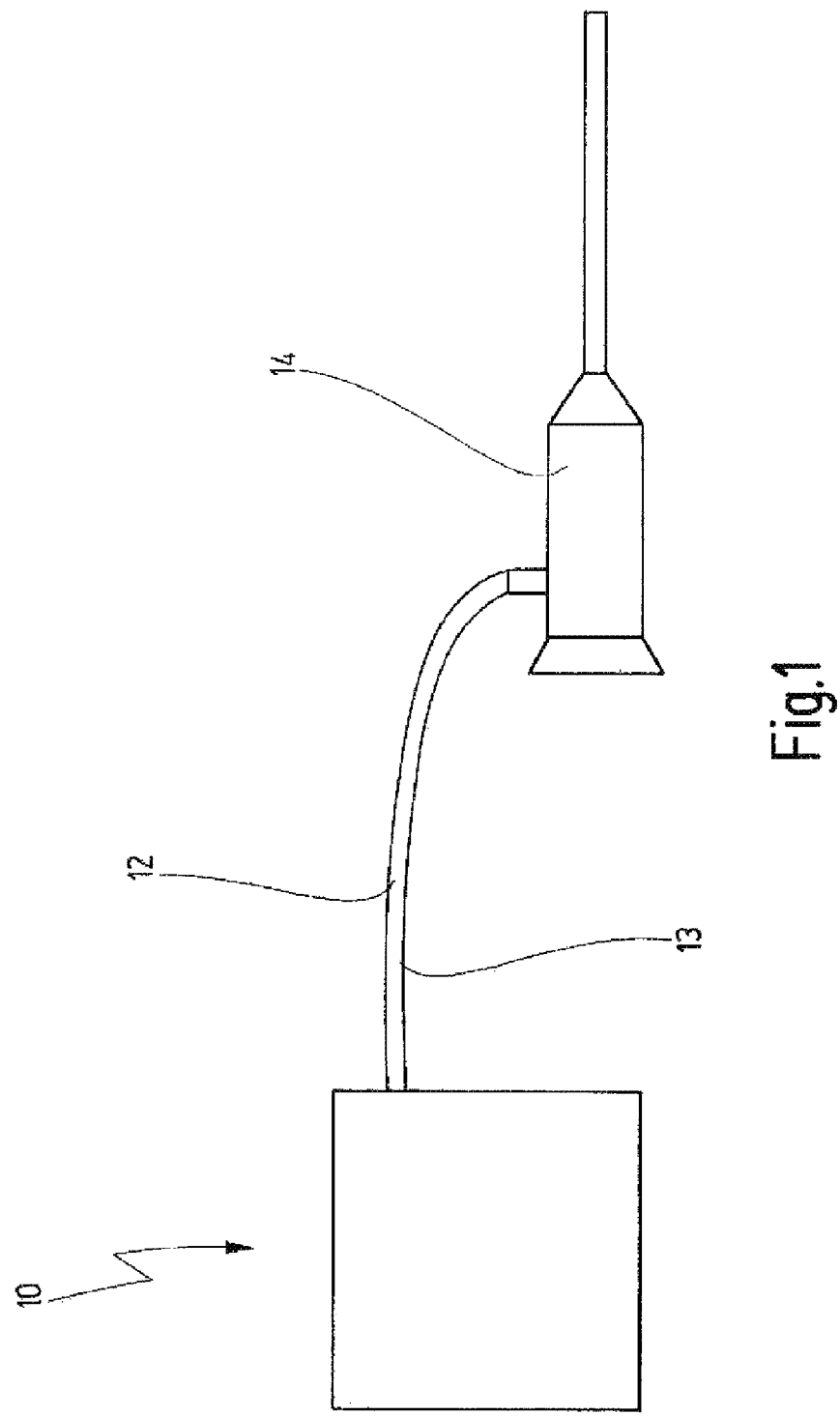
FIG. 1 shows an illumination device according to the invention connected to an endoscope.

FIG. 1 illustrates an illumination device provided with the general reference symbol 10.

By way of example, the illumination device 10 can be used in the field of microscopy or endoscopy in order to illuminate a region to be observed.

As illustrated in FIG. 1, the illumination device 10 can be connected to an endoscope 14 (as an observation device) by means of a light conducting cable 12, so that the light generated by the illumination device 10 is guided via the light conducting cable 12 to light conducting optics (not illustrated) of the endoscope 14. The illumination device 10 can also be arranged directly on an appropriate connector of the endoscope 14, for example via a plug connection; as a result of this, the light generated by the illumination device 10 can be directly coupled into the light conducting optics of the endoscope 14.

Figure 2:
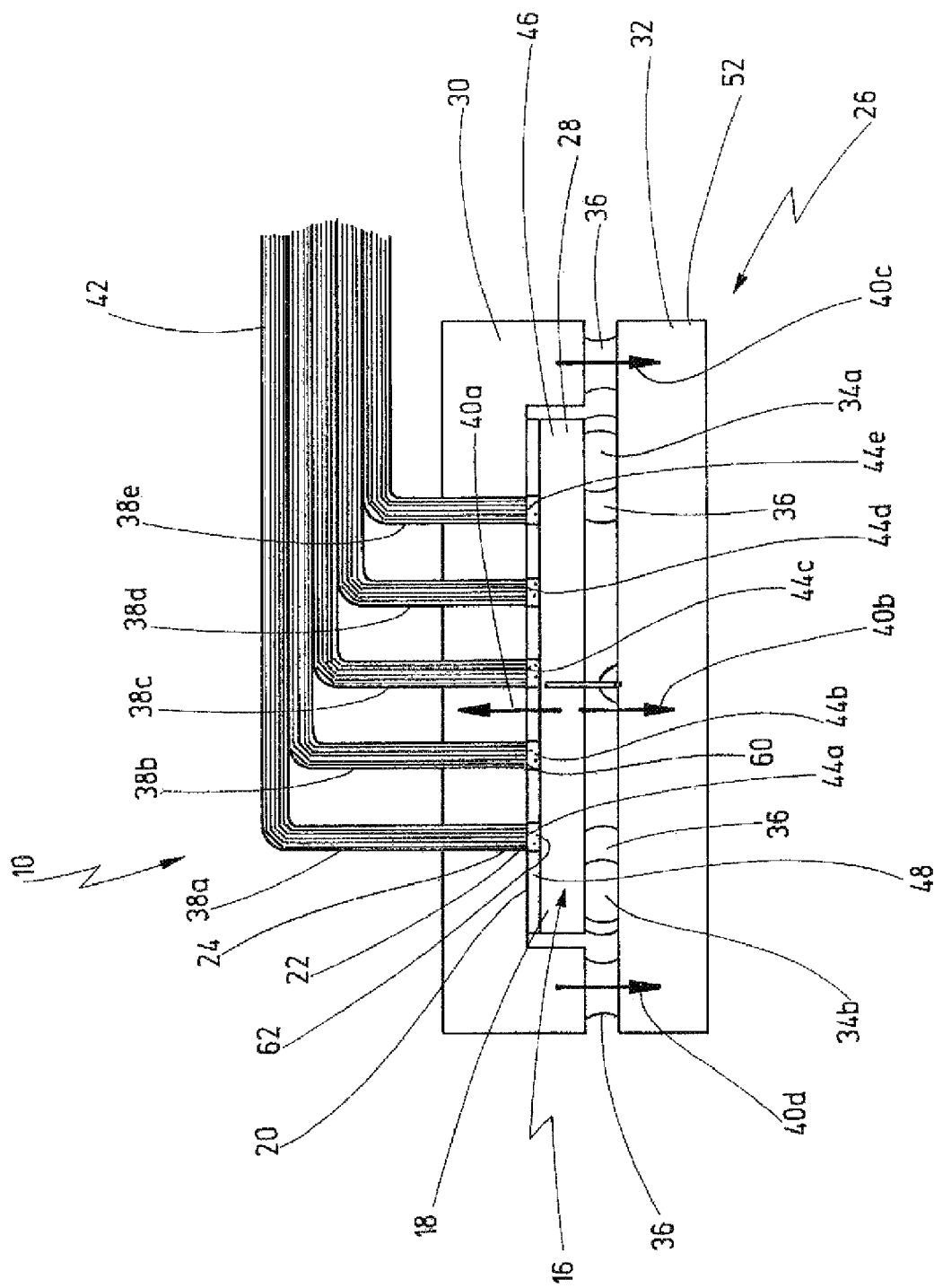
FIG. 2 shows an exemplary embodiment of the illumination device according to the invention shown in FIG. 1.

The illumination device 10 has a light source 16 in the form of at least one LED 18 (cf. FIG. 2). Proximal ends 22 of optical waveguides 24 are arranged on a light emitting surface 20 of the LED 18 and guide the light generated by the LED 18 to a distal end (not illustrated) of the optical waveguide 24 and hence to the light conducting cable 12 or directly to the endoscope 14.

The illumination device 10 furthermore comprises a cooling device 26 having a first and a second cooling element 28, 30, and a cooling body 32 in order to remove the heat generated by the LED 18 and cool the illumination device 10. The first cooling element 28 is arranged on a side of the light source 16 which faces away from the proximal ends 22 of the optical waveguides 24, whereas the second cooling element 30 is arranged adjacent to the light emitting surface 20 of the LED 18. The cooling body 32 is also, like the first cooling element 28, arranged on the side of the light source 16 which faces away from the proximal ends 22 of the optical waveguides 24, and, at the same time, it is arranged adjacent to the first cooling element 28. The cooling body 32 can also be arranged on the side of the LED 18 which faces the proximal ends 22 of the optical waveguides 24, or else it can be arranged at a distance from the cooling elements 28, 30. Furthermore, the first and second cooling elements 28, 30 and the cooling body 32 are connected together in a thermally conducting fashion. To this end, the first cooling element 28 is connected to an end face of the cooling body 32, which faces the first cooling element 28, by means of a solder drop 34 and a thermally conducting adhesive 36, and moreover the edge region of the second cooling element 30 is adhesively connected to the cooling device 26 by means of the thermally conducting adhesive 36. It follows that the heat generated by the LED 18 is dissipated in the direction of the arrows 40a, b to the second and first cooling element 30, 28, respectively. The second cooling element 30 transfers the absorbed heat to the cooling body 32 via its edge region, in the direction of arrows 40c, d. The first cooling element 28 transfers the heat it absorbs to the cooling body 32 via the solder drop 34 and the thermally conducting adhesive 36.

Furthermore, the cooling body 32 can be connected to a housing wall (not illustrated) of the illumination device 10 so that the heat generated by the LED 18 can be dissipated effectively and no accumulation of heat occurs within the illumination device 10.

The optical waveguides 24 formed from glass fibres are connected in the region of the second cooling element 30 to form optical waveguide bundles 38—here five optical waveguide bundles 38a-e are illustrated—which pass through the second cooling element 30 at a distance from one another and at an angle of approximately 90° to the surfaces of the second cooling element 30. The optical waveguide bundles 38a-e are furthermore arranged at a distance from one another on the light emitting surface 20 of the LED 18. The heat emitted by the light emitting surface 20 of the LED 18 to the proximal ends 22 of the optical waveguides 24 of the optical waveguide bundles 38a-e is thus dissipated by the second cooling element 30; as a result of this, a particularly efficient cooling of the illumination device 10 is achieved.

On the distal side of the second cooling element 30, the optical waveguide bundles 38a-e are connected to form a common fibre optic loom 42. To this end, the optical waveguide bundles 38a-e, which are offset with respect to one another and pass approximately perpendicularly through the second cooling element 30, are bent by approximately 90° such that the proximal ends 22 of differing lengths of the optical waveguides 24 of the optical waveguide bundles 38a-e of the fibre optic loom 42 run parallel with respect to one another.

Figure 3:
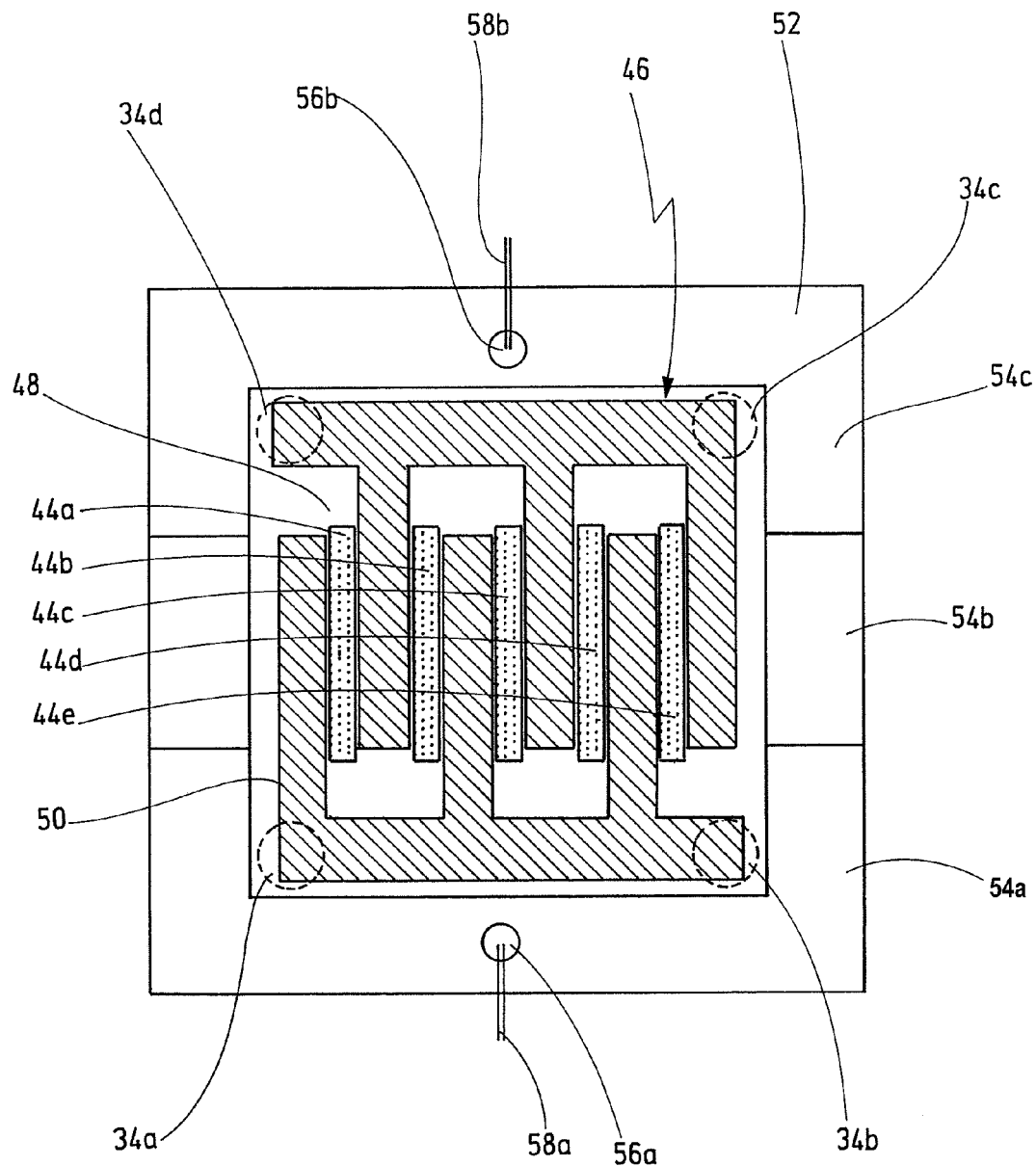
FIG. 3 shows a plan view of an LED of the illumination device according to the invention shown in FIG. 2.

With reference to FIG. 3, the LED 18 is affixed on a carrier structure 46, e.g. a chip. The light emitting surface 20 of the LED 18 has regions with a high light emission intensity 44a-e, represented by the dotted areas, and regions with a low or average light emission intensity 48. The regions with a low or average light emission intensity 48 are formed in part by the arrangement of electrical supply structures 50a, b for the LED 18, which run along end regions of the light emitting surface 20 of the LED 18 and between the regions with a high light emission intensity 44a-e.

The carrier structure 46 is arranged on a quadrilateral substrate 52, which acts as the first cooling body 28 and which has three sections 54a, c. The outer sections 54a, c are designed to be electrically conducting, whereas the central section 54b arranged between the two outer sections 54a-c is designed to be electrically insulating. A contact 56a, b is provided in each case on the electrically conducting sections 54a, c, and the electrical supply lines 58a, b for the LED 18 are arranged on the former. The solder drops 34—four solder drops 34a-d are illustrated here—are affixed between corner regions of the quadrilateral carrier structure 46 and the substrate 52.

Figure 4:
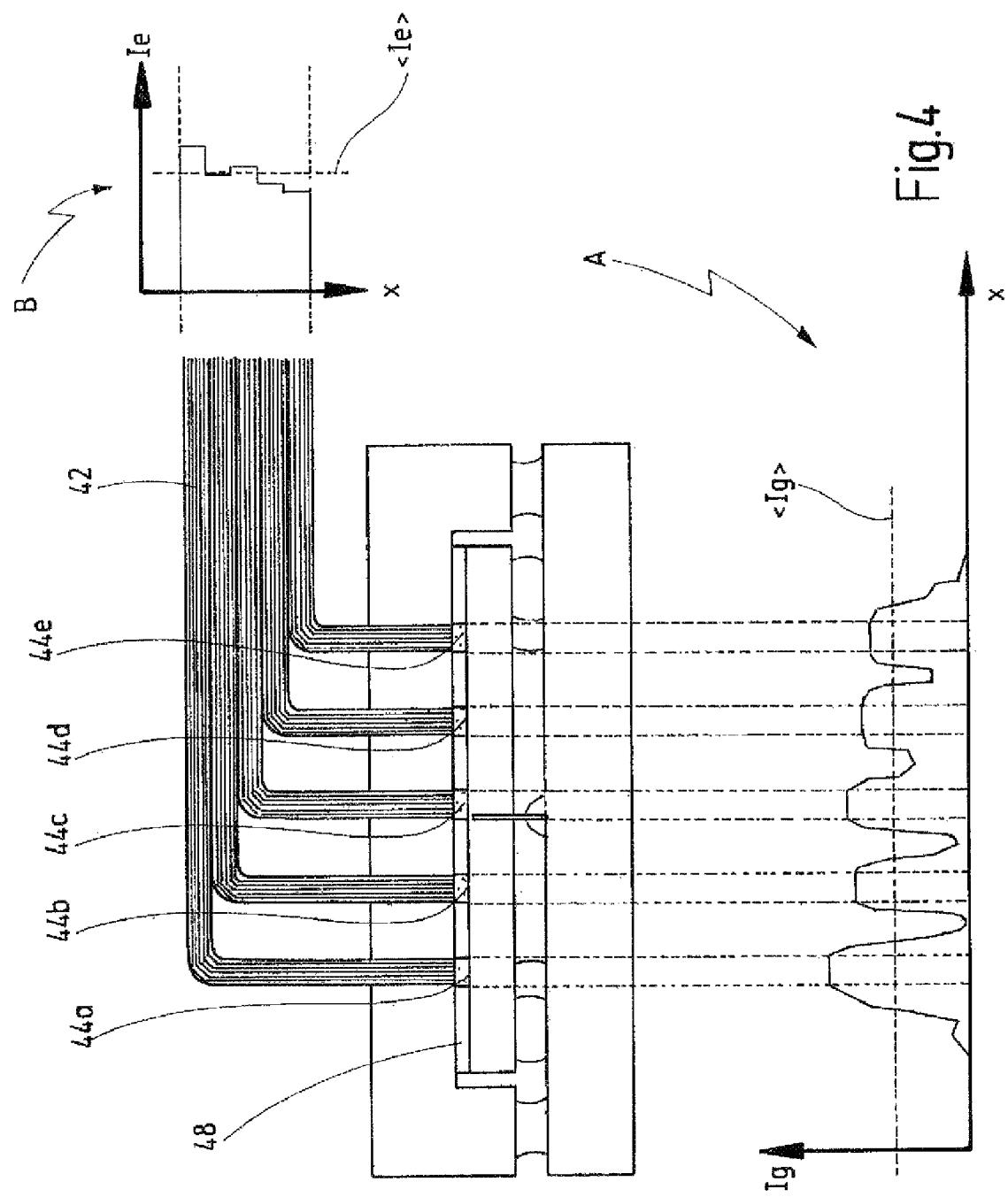
FIG. 4 shows light intensity profiles of the illumination device shown in FIG. 2.

Connecting the optical waveguide bundles 38a-e to the regions with a high light emission 44a-e of the LED 18 leads to an increase in the light intensity of the illumination device 10. Diagram A in FIG. 4 shows the profile of the light intensity $I_g$ of the LED 18 which can be coupled in as a function of a position x on the light emitting surface 20 of the LED 18. The light intensity profile, illustrated by means of a solid line, shows local light intensity maxima which are located in the region where the optical waveguide bundles 38a-e are arranged in the regions with a high light emission intensity 44a-e, and which decrease in the direction of intermediate regions which are formed by regions with an average or low light emission intensity 48. The regions with an average or low light emission intensity 48 in general have a low light intensity value. The average value of the light intensity $<I_g>$, illustrated by the dashed line, results from averaging over all light intensities along the position x on the surface 20 of the LED 18. Diagram B in FIG. 4 shows the profile of the light intensity $I_l$, as a function of the fibre optic loom 42 formed by the optical waveguide bundles 38a-e. Due to the fact that only regions with a high light emission intensity 44a-e are connected to the optical waveguide bundles 38a-e, an average value of the light intensity $<I_l>$ across the cross section of the fibre optic loom 42 is greater than the average value of the light intensity $<I_g>$ along the entire light emitting surface 20 of the LED 18. Thus, the light guided to the endoscope 14 is concentrated, despite a loss of light intensity of the light source 18, so that the light intensity of the illumination device 10 and thus its brightness is significantly increased.

Referring back to FIG. 2, the proximal ends 22 of the optical waveguide bundles 38a-e are arranged directly on the light emitting surface 20 of the LED 18. In this context, a direct arrangement of the optical waveguide bundles 38a-e on the LED 18 is understood to be an arrangement without additional optical elements in the form of lenses, fibre cones, etc. The proximal ends 22 of the optical waveguides 24 of the optical waveguide bundles 38a-e can for example be arranged directly on the light emitting surface 20 of the LED 18, or else be at a short distance therefrom. The direct arrangement of the optical waveguide bundles 38a-e on the regions with a high light intensity 44a-e can be realized by pressing or adhesive bonding, for example.

Figure 5A:
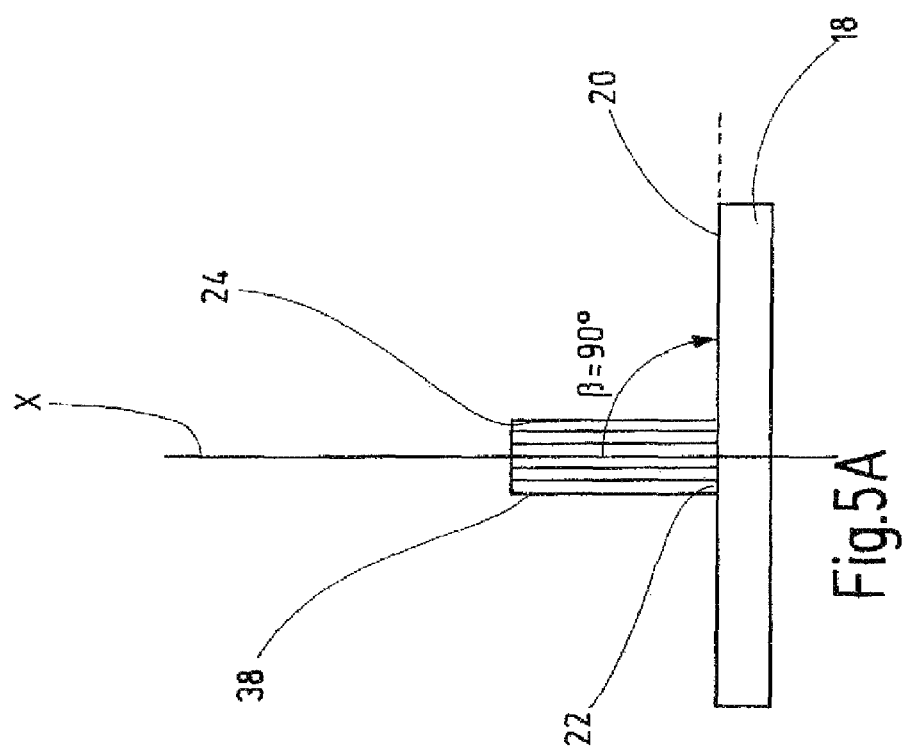
FIG. 5A shows a schematic illustration of light being coupled into an optical waveguide bundle arranged directly on a light source.
Figure 5B:
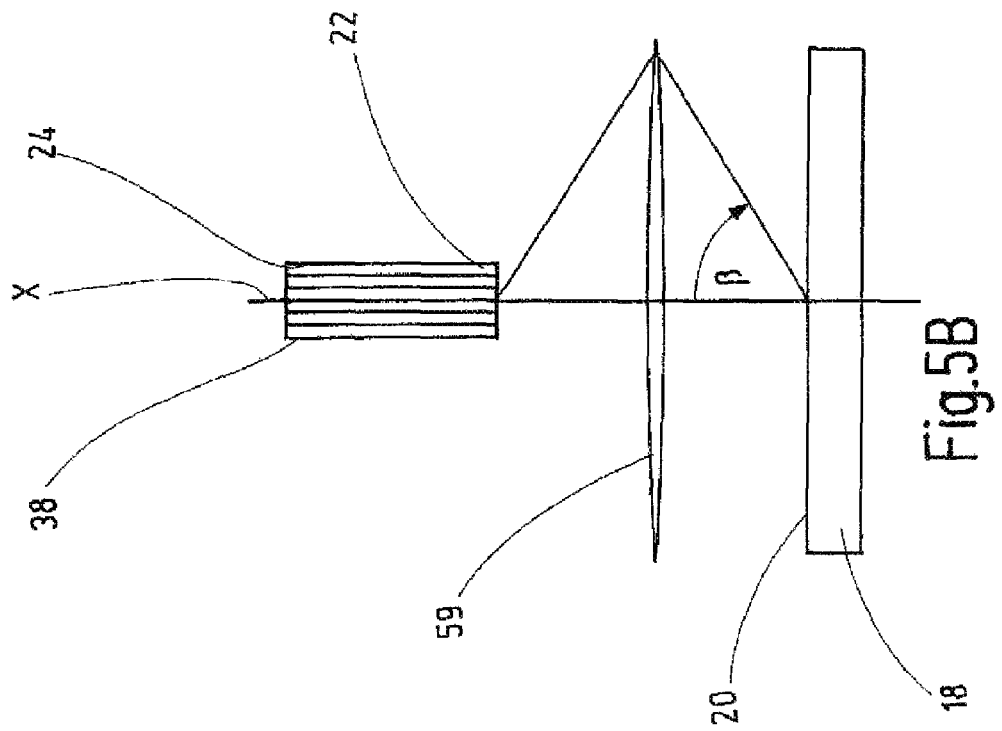
FIG. 5B shows a schematic illustration of light being coupled into an optical waveguide bundle via a lens.

As illustrated in FIG. 5A, a minimum angle of incidence of 0° (corresponding to β=90° in FIG. 5A) can be selected due to the direct arrangement of the optical waveguide bundle 38 on the surface 20 of the LED 18. Here, β refers to the angle between the propagation direction of the light and a longitudinal direction X of the optical waveguide bundle 38 which is arranged on a surface 20 of the LED and into which the light is intended to be coupled in. If the optical waveguide bundle 38 is arranged directly on or at a short distance from the surface 20 of the LED 18, all of the emitted light is coupled into the optical waveguide bundle 38, independent of the propagation direction of the light. This additionally increases the maximum light intensity of the illumination device 10. Furthermore, only the light of the corresponding LED section is coupled into the optical waveguide bundle 38 in the case of the direct arrangement of the optical waveguide bundle 38 on the LED 18, so that the light intensity of the optical waveguide bundle 38 per cross sectional area is additionally increased. If, on the other hand, optical elements (like a lens 59 illustrated in FIG. 5B) are used to focus the light emitted by the surface 20 of the LED 18, the angle β of the light is less than 90°. The coupling-in angle of the light accepted by the optical waveguide bundle 38 is determined by the design of the optical waveguide 24 and can furthermore be optimized by the choice of material and the production process of the optical waveguides 24.

In the case of the optical waveguide bundles 38a-e being arranged at a short distance, as is illustrated in an exemplary manner for the optical waveguide bundle 38b in FIG. 2, the proximal end 22 of the optical waveguides 24 of the optical waveguide bundle 38b preferably has an antireflection coating 60 which additionally increases the light intensity of the light which is coupled into the proximal ends 22 of the optical waveguides 24 of the optical waveguide bundle 38b.

Moreover, a light modulation layer 62 is arranged on the light emitting surface 20 of the LED 18, which can change a property (in this case the light wavelength) of the light generated by the LED 18. For example, in the case of an LED 18 emitting blue light, the light modulation layer 62 can be designed as a phosphorous layer, so that the blue light emitted by the LED 18 is converted into white light. Here, the light modulation layer 62 is arranged in the region of the proximal ends 22 of the optical waveguides of the optical waveguide bundles 38a-e, that is to say in the regions with a high light emission intensity 44a-e. The light modulation layer 62 can also be arranged over the entire extent of the light emitting surface 20 of the LED 18.

Figure 6:
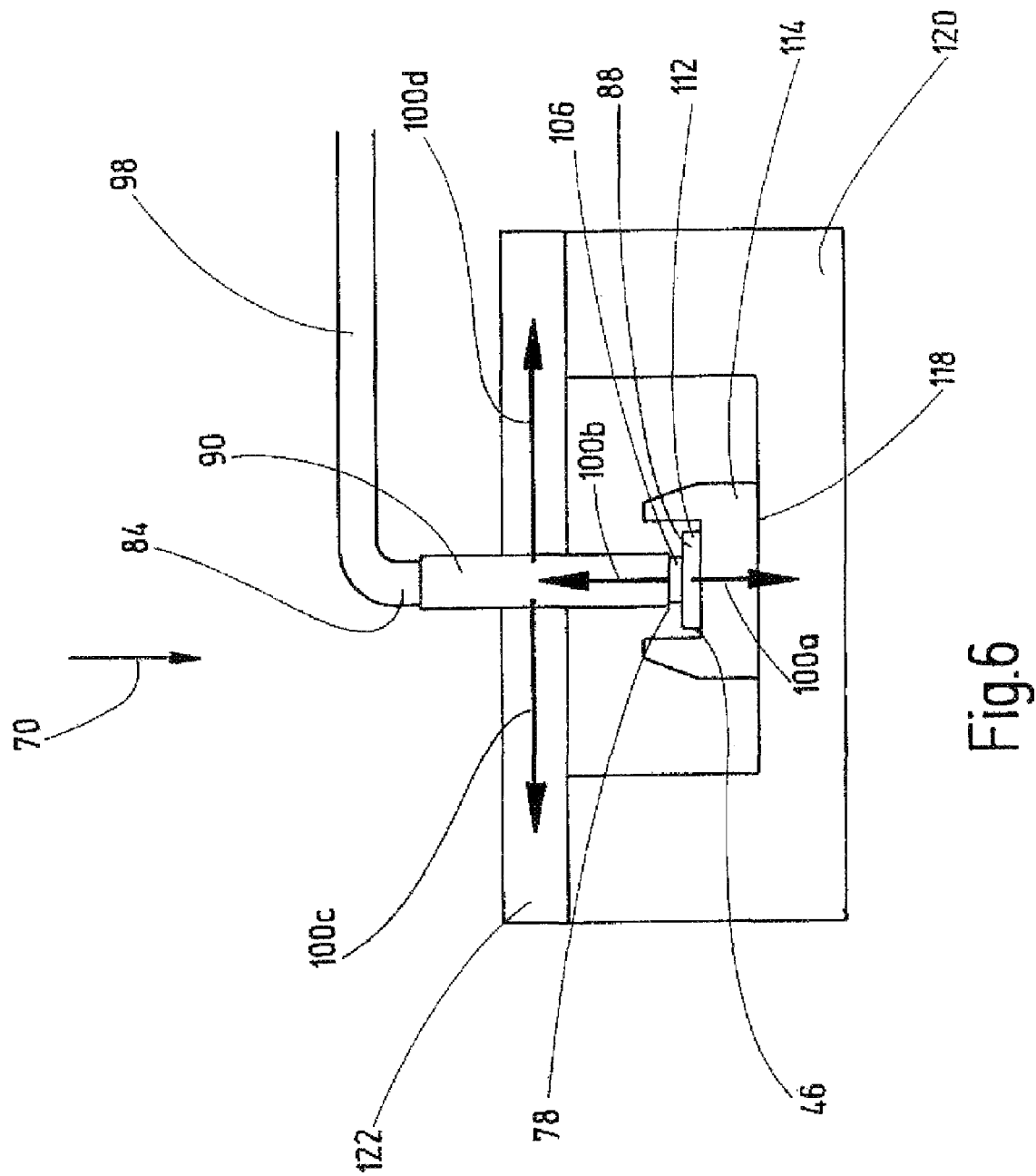
FIG. 6 shows a further exemplary embodiment of the illumination device according to the invention shown in FIG. 1.
Figure 7:
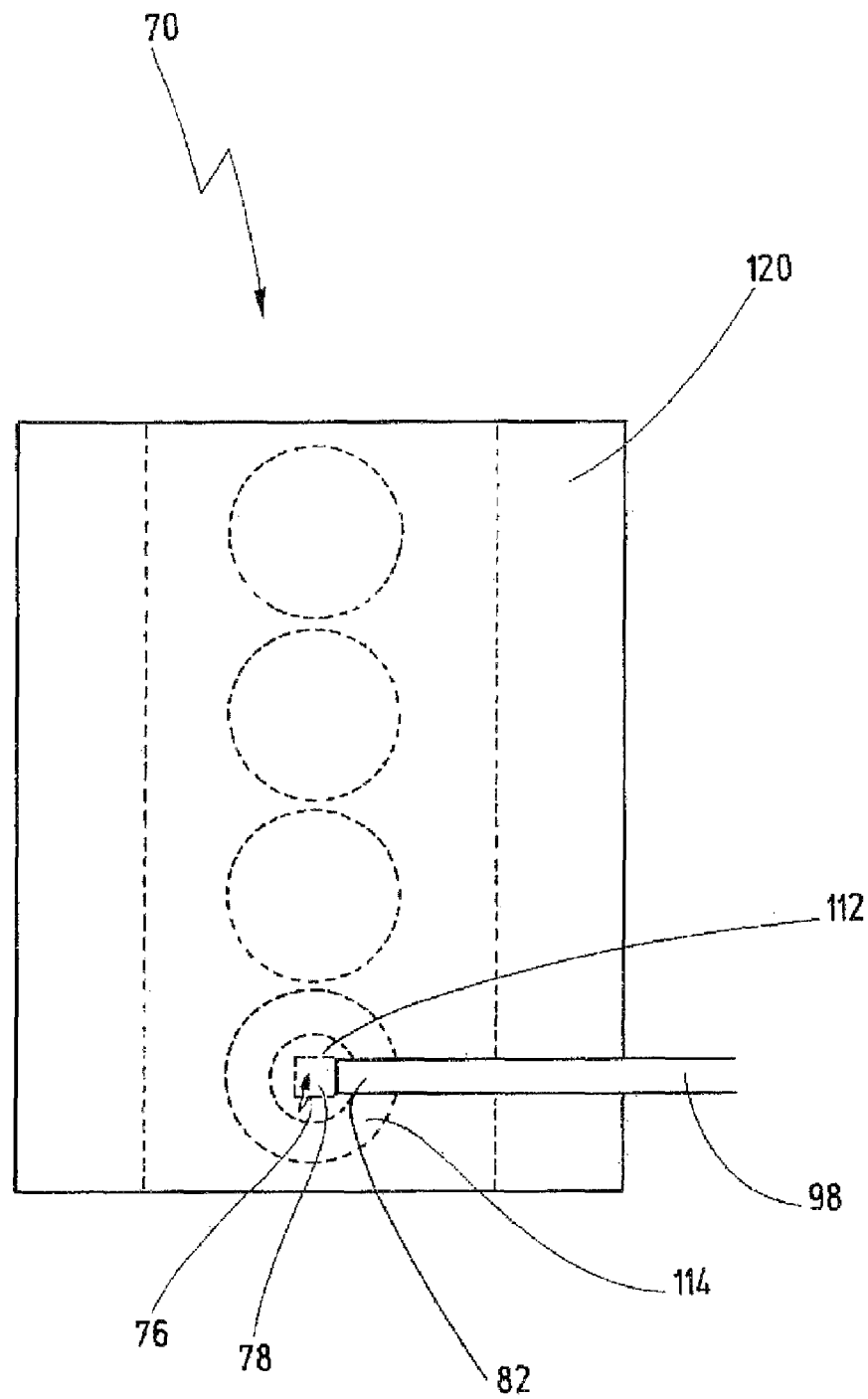
FIG. 7 shows a plan view of the illumination device according to the invention shown in FIG. 5.

FIGS. 6 and 7 illustrate a further illumination device 70, in which features of the illumination device 70 which are identical to the features of the illumination device 10, or which correspond thereto, are provided with reference symbols whose value has been increased by 60.

The illumination device 70 in FIG. 6 has a light source 76 with an LED 78 on a carrier structure 106.

The carrier structure 106 is connected via its underside to a substrate 112, which acts as a first cooling element 88 and is arranged in a recess 116 of a cooling body 114 comprising, for example, solid metal. A material of the substrate 112 has a thermal expansion coefficient which compensates the thermal expansion of the carrier structure 106. Additionally, an underside 118 of the metal cooling body is connected to a bowl-shaped or trough-shaped assembly body 120 of the illumination device 70. Furthermore, a cover 122 is arranged on an upper end face of the assembly body 120 and the second cooling element 90 passes through the former. The second cooling element 90 is designed as a fibre body with thin copper-rib structures. An optical waveguide bundle 98 made of optical waveguides 84 formed from fibreglass passes through the second cooling element 90, the proximal ends 82 of the former being connected to areas with a high light emission from the light emitting surfaces of the LED 78. Furthermore, the proximal ends 82 of the optical waveguides 84 of the optical waveguide bundle 98 are arranged directly on a surface of the LEDs.

The heat generated by the light source 76 is transferred to the assembly body 120 along the arrows 100a-d. The first cooling element 88 emits the absorbed heat via the cooling body 114 to the assembly body 120. The second cooling element 90 absorbs the heat from the LED 78 and transfers it to the assembly body 120 via the cover 122. Hence, sufficient cooling of the illumination device 70 is achieved.

If FIG. 7 is considered to be a plan view, FIG. 6 corresponds to a vertical section. FIG. 7 shows a number of units, comprising the LED, the first and second cooling elements, the optical waveguide bundle, etc., assembled on the assembly body 120, with only one such unit being shown in detail.

Figure 8:
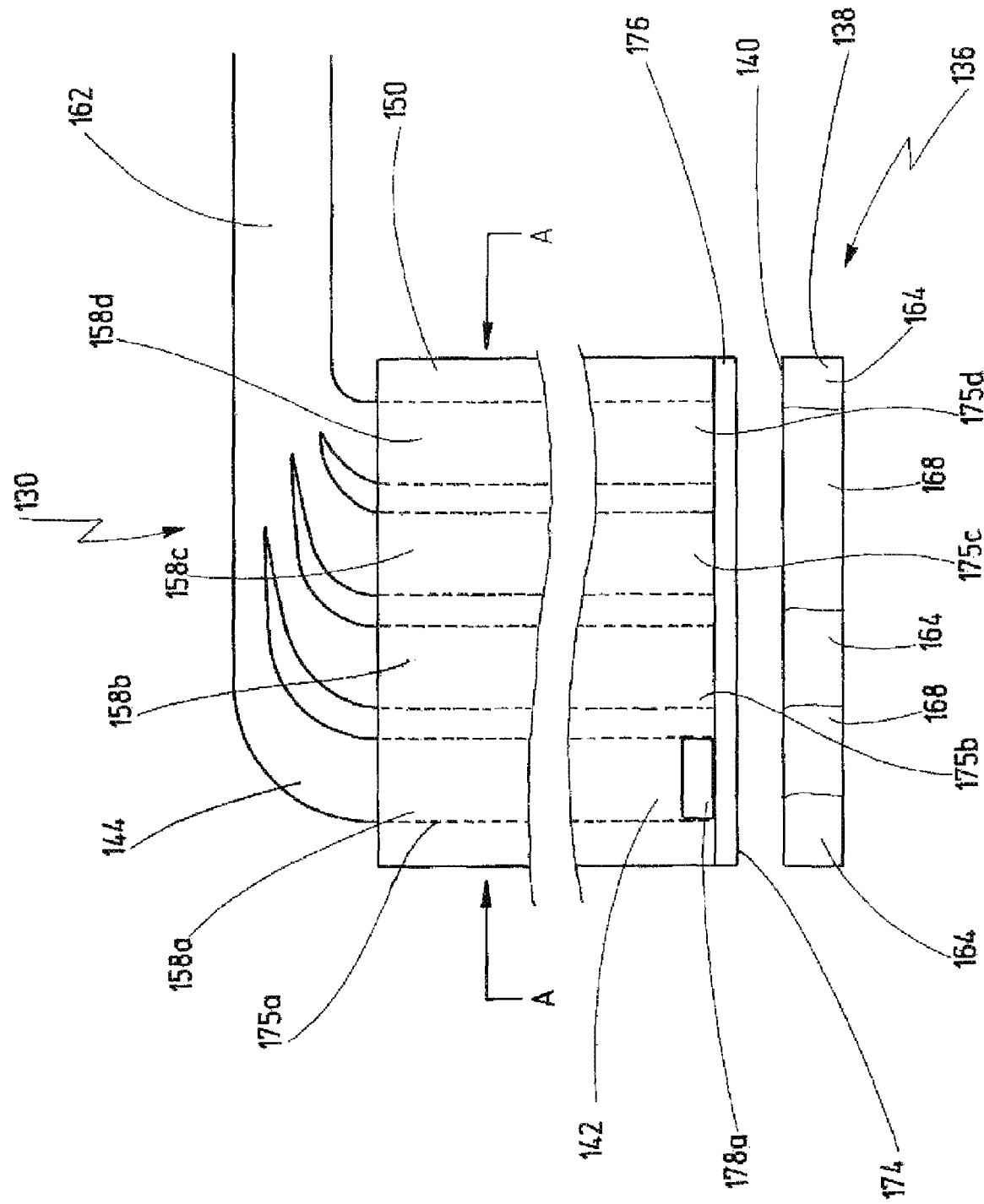
FIG. 8 shows an additional exemplary embodiment of the illumination device according to the invention shown in FIG. 1.
Figure 9:
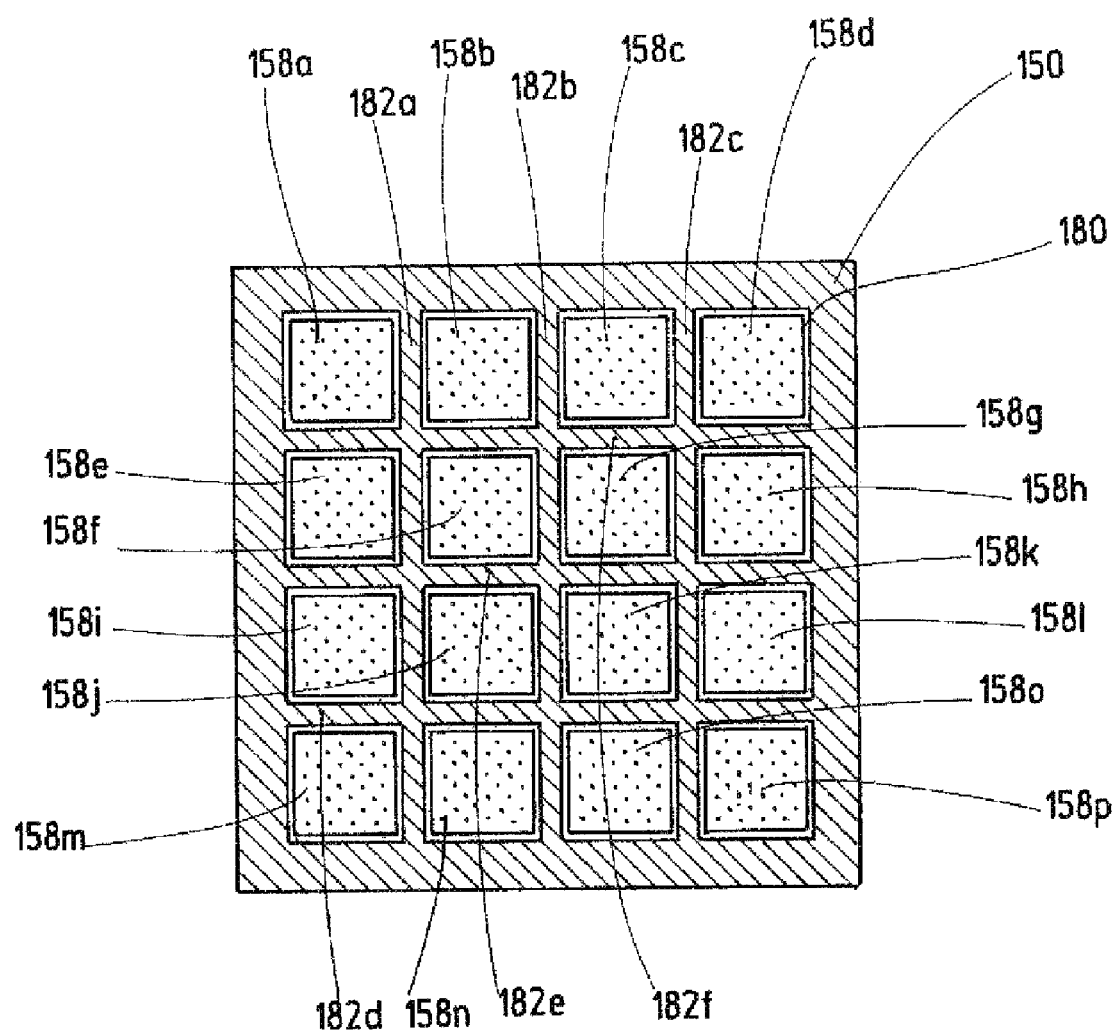
FIG. 9 shows a plan view of the illumination device shown in FIG. 8.

FIGS. 8 and 9 illustrate a further illumination device 130, in which features of the illumination device 130 which are identical to the features of the illumination device 10, or which correspond thereto, are provided with reference symbols whose value has been increased by 120.

A light source 136 of the illumination device 130 is designed as an LED 138. A second cooling element 150 is directly contacted by the light emitting surface 140 of the LED 138, or is arranged at a short distance therefrom, so that an air gap is present between the surface 140 of the LED 138 and an end face 174 of the second cooling element 150. The second cooling element 150 is made of a thermally conducting material which has passages 175a-d, through which the optical waveguide bundles 158 (four optical waveguide bundles 158a-d in FIG. 7) pass.

FIG. 9 shows a cross section through the second cooling element 150 along the line A-A in FIG. 8, through which the proximal ends 142 of the optical waveguides 144, combined to form optical waveguide bundles 158a-p, pass. Here, the optical waveguide bundles 158a-p have an approximately quadrilateral cross section so that, as a result of the additional regular arrangement of the optical waveguide bundles 158a-p, a maximum number of optical waveguide bundles 158a-p can be passed through the second cooling element 150. The cross section of the optical waveguide bundles 158a-p can also have any regular shape (e.g. trapezoidal, rectangular, circular) or an irregular shape. The optical waveguide bundles 158a-p are provided with a cladding 180 which protects the outer surfaces of the optical waveguide bundles 158a-p from damage and is used as a joint to the second cooling element 150. The cladding 180 is designed to be thermally conducting so that the heat transported by the optical waveguide bundles 158a-p can be transferred to the second cooling element 150 via the cladding 180. The second cooling element 150 has web-shaped structures 182a-f, which are orthogonal to one another, between the optical waveguide bundles 158a-p.

A heat diffusion element 176 is attached, e.g. by adhesive bonding, to the end face 174 of the second cooling element 150 which faces the light emitting surface 140 of the LED 138 so that it extends over the entire extent of the end face 174 (cf. FIG. 8). The heat diffusion element can also be vapour deposited or applied in liquid form. The heat diffusion element 176 is transparent to light and designed to be antireflective, if required, so that the light emitted by the LED surface 140 is transmitted through the heat diffusion element with as little loss as possible. Furthermore, the heat diffusion element is produced from such a material that it absorbs the heat emitted by the LED 138 and transfers it into the second cooling element 150.

Furthermore, heat absorption elements 178 can be inserted into the proximal ends 142 of the optical waveguide bundles 158a-d; in this case, a heat absorption element 178a is illustrated schematically for the optical waveguide bundle 158a. The heat absorption elements 178 are arranged directly adjacent to the heat diffusion element 176 so that corresponding end faces touch. The heat absorption elements 178 comprise a material transparent to light, for example diamond or sapphire; as a result of this they absorb the heat which is generated by the light emitting surface 140 of the LED 138 and enters the proximal end 142 of the optical waveguide bundles 158, due to their relatively high thermal conductivity, and transfer it to the second cooling element 150 via their outer side. Hence, optimum cooling of the optical waveguide bundles 158 is achieved.

In the exemplary embodiment shown, the optical waveguides 144 of the optical waveguide bundles 158a-p are designed as optical waveguides formed from glass fibres. It is also possible for the optical waveguides 144 to be designed as liquid optical waveguides. In this case, a liquid flowing through the optical waveguide 144 has a relatively high refractive index, whereas the material of the outer walls of the optical waveguides 144 has a relatively low refractive index on the surface. Moreover, the material of the outer walls of the optical waveguides 144 is designed to be transparent to light, so that the liquid optical waveguide 144 has the desired dielectric properties with regard to reflection. It is also possible that the passages 175a-d of the second cooling element 150 are designed as inlet and outlet lines for a liquid which is transparent to light. The liquid can circulate along the light emitting surface 140 of the LEDs 138 so that the light source 136 is additionally cooled. It is also possible for the outer walls of the optical waveguide 144 to have a metallic silvering so that the guiding of the light is increased due to total internal reflection in the optical waveguides 144.

The optical waveguides 144 are arranged along the entire light emitting surface 140 of the LED 138 so that the proximal ends 142 of the optical waveguides 144 of the optical waveguide bundles 158 are arranged both at regions with a high light emission intensity 164 and at regions with an average or low light emission intensity 168. Only those optical waveguides 144 which are connected to the regions with a high light emission intensity 168 are used to provide light. The optical waveguides 144 connected to the regions with an average or low light emission intensity 168 are used, for example, for effect lighting or functional display of the illumination device 130 which is attached to an outer housing wall, e.g. the front panel, of the illumination device 130. The optical waveguides 144 arranged on the regions with an average or low light emission intensity 168 can also be bent without them being used to guide the light.

In order to increase the light intensity, a distal end 184 of the optical waveguides 144 is fused or pressed so that transition areas between the optical waveguides 144 are reduced. An end face of the distal end of the fibre optic loom 160 is moreover provided with an antireflection coating 186 in order to reduce the loss when light is coupled out of the fibre optic loom 160.

Figure 10:
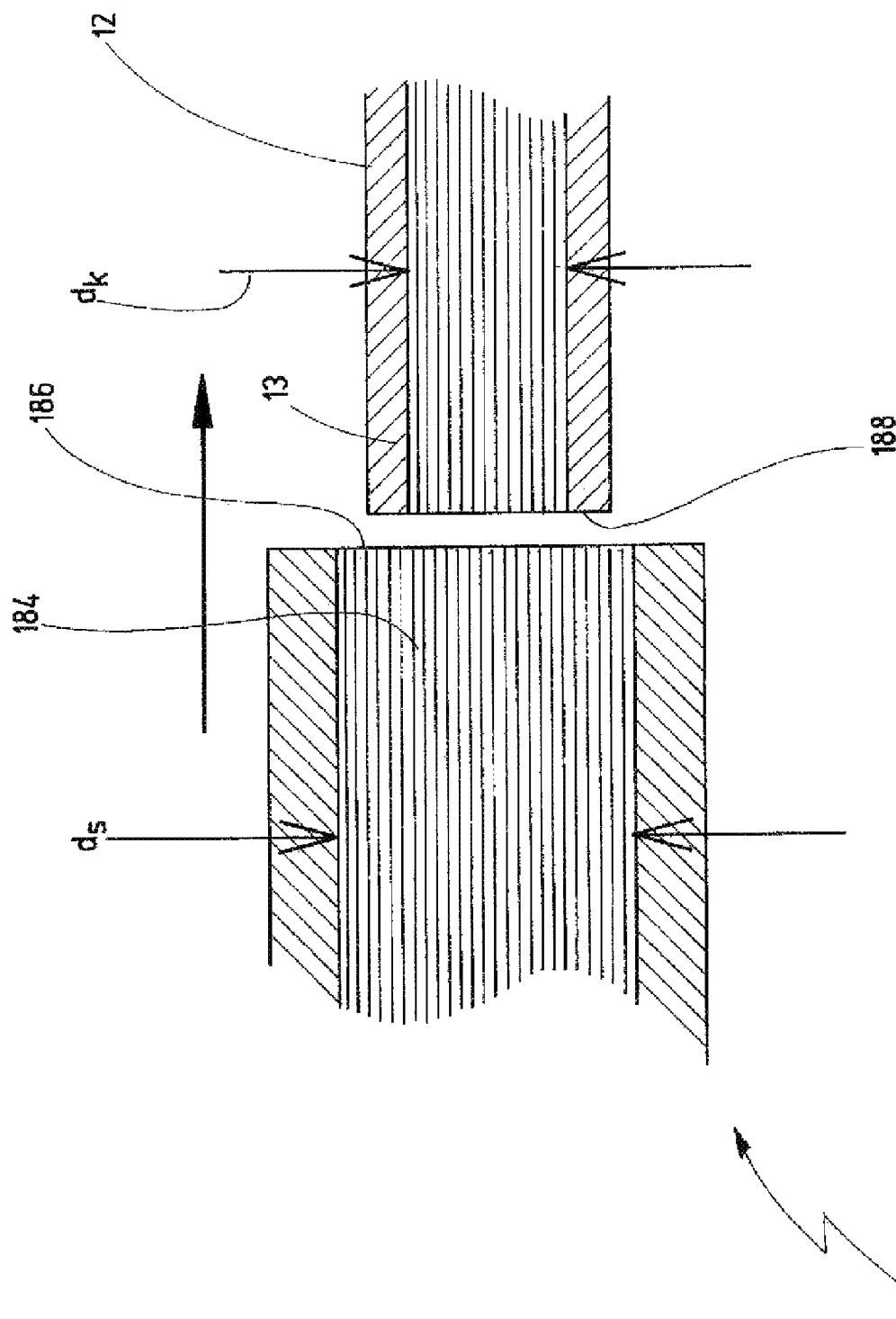
FIG. 10 shows the distal end of a fibre optic loom which can be connected to a light conducting cable.
Figure 11:
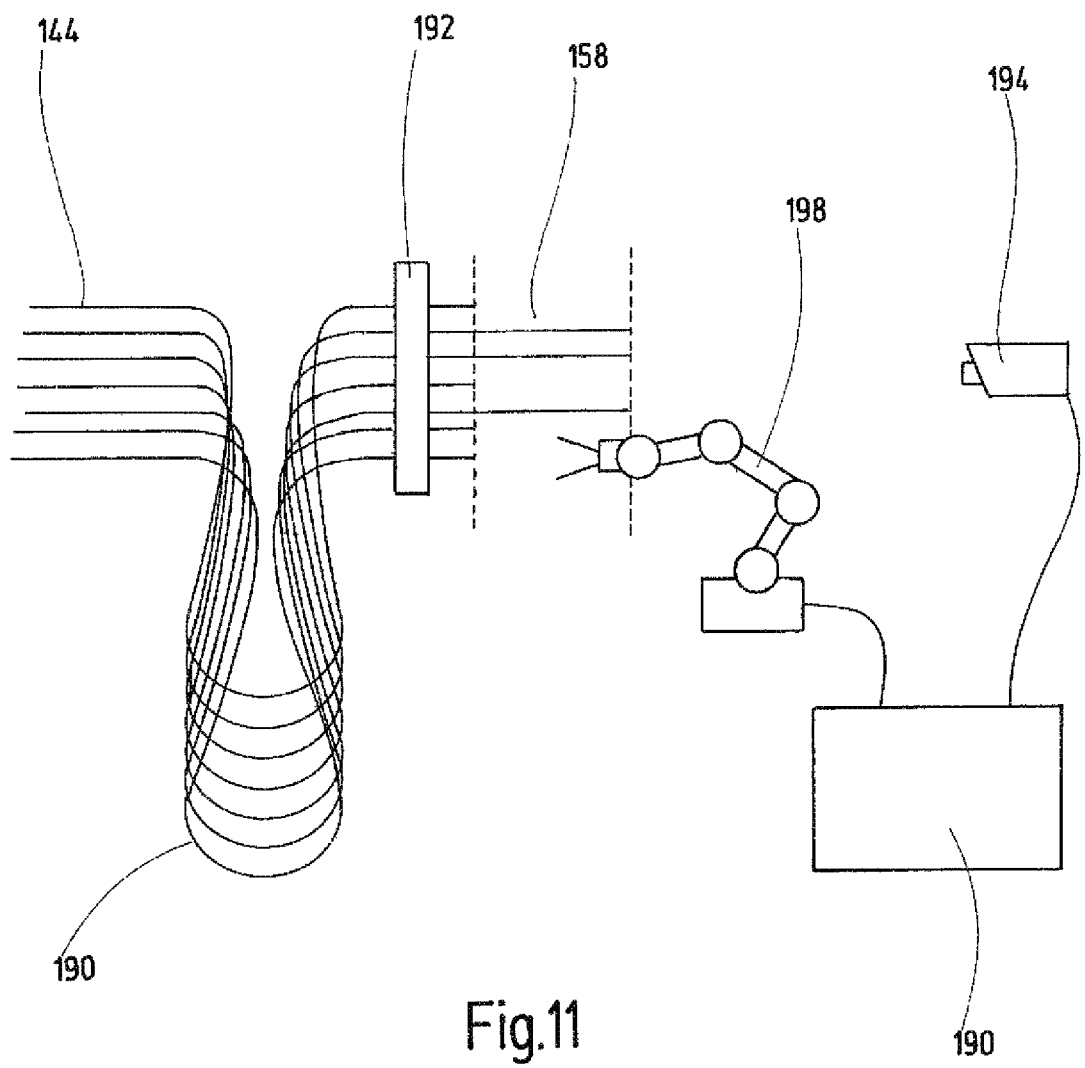
FIG. 11 shows a schematic illustration of a production of the illumination device according to the invention shown in FIG. 1.

In order to increase the coupling-in efficiency between the fibre optic loom 160 and the light conducting cable 12, which leads from the endoscope to the illumination device 130, provision is furthermore made for a diameter $d_s$ of the fibre optic loom 160 to be slightly larger than a diameter $d_k$ of the light conducting cable 12 (cf. FIG. 10). As a result of this, the greatest amount of light intensity is transmitted from the fibre optic loom 160 to the light conducting cable 12. It is also possible that, in order to match the refractive indices of the fibre optic loom 160 and the light conducting cable 12, provision is made for a means for balancing the refractive indices of the optical waveguides 144 of the fibre optic loom 160 and the light conducting cable 12; for example, provision is made for a transparent elastomer which reduces reflection losses in the light intensity in the transfer from fibre optic loom 160 into the light conducting cable 12. Moreover, the proximal end 13 of the light conducting cable 12 is provided with an antireflection coating 188. Additionally, a gap between the fibre optic loom 160 and light conducting cable 12 should be as small as possible.

FIG. 10 illustrates a production step of the illumination device 10, in which optical waveguides are selected in order to be able to arrange the optical waveguides 144 on the regions with a high light emission intensity 164 and the regions with a low light emission intensity 168. The optical waveguides 144 pass over a compensation loop 190 to a fibre clamp 192, by means of which the optical waveguides 144 are held fanned out and parallel to one another. A camera 194 which is connected to a control unit 196 selects the optical waveguides 144 according to their light intensity in order to select those optical waveguides 144 which are connected to the regions with a high light emission 164. A robotic arm 198 connected to the control unit 196 grips those optical waveguides 144 which are connected to the regions with a high light emission intensity 164 and spatially separates them from the other optical waveguides 144. The selected optical waveguides 144 are pulled forward whilst under slight friction so that they can be combined to form optical waveguide bundles 158 which are connected to the light conducting cable 12.

What is claimed is:

1. An illumination device for generating light and supplying said light to an observation device used in endoscopy or microscopy, comprising:
    a light source having at least one LED,
    one or more optical waveguides having a proximal end and a distal end, said proximal end being arranged on a side of said light source which faces said optical waveguide,
    a cooling device to dissipate heat generated by said light source, wherein said cooling device has
        at least one first cooling element for dissipating heat generated by said light source, said at least one first cooling element being arranged on a side of said light source which faces away from said proximal end of said optical waveguide, and
        a second cooling element for dissipating heat generated by said light source, said second cooling element being arranged on a side of said light source which faces said proximal end of said optical waveguide, said one or more optical waveguides passing through said second cooling element.

2. The illumination device of claim 1, wherein each of said one or more optical waveguides is an optical waveguide, wherein each of said one or more optical waveguides pass through said second cooling element, wherein each of said one or more optical waveguides are arranged at a distance from one another in a region of said second cooling element.

3. The illumination device of claim 2, wherein distal ends of each of said one or more optical waveguides are fused together.

4. The illumination device of claim 1, wherein each of said one or more optical waveguides is arranged in regions of said light source, which emit a high light emission intensity.

5. The illumination device of claim 1, wherein each of said one or more optical waveguides is arranged in first regions of said light source, which first regions emit a high light emission intensity, and in second regions of said light source, which second regions emit a low or average light emission intensity, wherein each of said one or more optical waveguides arranged in said first regions emitting a high light emission intensity is able to be connected to a proximal end of a light conducting cable or to an observation device.

6. The illumination device of claim 1, wherein each of said one or more optical waveguides is designed as at least one of optical fibres, liquid optical waveguides, solid light conducting elements without an inner structure, in a region of said second cooling element.

7. The illumination device of claim 1, wherein said second cooling element comprises, at least along part of a side of said second cooling element which faces said light source, a heat defusion element for dissipating heat generated by said light source into said second cooling element.

8. The illumination device of claim 1, wherein each of said one or more optical waveguides has a heat absorption element which dissipates heat of each of said one or more optical waveguides and which is inserted into each of said one or more optical waveguides on said proximal end of each of said one or more optical waveguides.

9. The illumination device of claim 1, wherein each of said one or more optical waveguides has an approximately quadrilateral cross-section.

10. The illumination device of claim 1, wherein said first cooling element and said second cooling element are connected with one another in a thermally conducting fashion.

11. The illumination device of claim 1, wherein said proximal end of each of said one or more optical waveguides is arranged directly on said light source.

12. The illumination device of claim 1, wherein said proximal end of each of said one or more optical waveguides is arranged at a short distance from said light source.

13. The illumination device of claim 1, wherein an optical contact element is arranged between said proximal end of each of said one or more optical waveguides and said light source.

14. The illumination device of claim 1, wherein said distal end of each of said one or more optical waveguides has an antireflection coating.

15. The illumination device of claim 1, wherein a transparent coupling elastomer is inserted between said distal end of each of said one or more optical waveguides and a proximal end of a light conducting cable or an observation device.

16. The illumination device of claim 1, wherein said light source comprises a plurality of LEDs.

17. An illumination device for generating light and supplying said light to an observation device used in endoscopy or microscopy, comprising a light source having at least one LED, at least one optical waveguide having a proximal end and a distal end, said proximal end being arranged on a side of said light source which faces said optical waveguide, a cooling device to dissipate heat generated by said light source, wherein said cooling device has at least one first cooling element for dissipating heat generated by said light source, said at least one first cooling element being arranged on a side of said light source which faces away from said proximal end of said optical waveguide, and a second cooling element for dissipating heat generated by said light source, said second cooling element being arranged on a side of said light source which faces said proximal end of said optical waveguide, said at least one optical waveguide passing through said second cooling element, wherein said light source, at least in part, has a light modulation layer on a side which faces said proximal end of said at least one optical waveguide for modulating a property of light emitted by said light source.

18. The illumination device of claim 17, wherein said at least one optical waveguide is arranged in regions of said light source, which regions emit a high light emission intensity and wherein said light modulation layer is arranged in said regions which emit a high light emission intensity.

19. The illumination device of claim 17, wherein said light modulation layer is thermally conducting.

20. The illumination device of claim 17, wherein said light modulation layer comprises a thermally conducting coating.

* * * * *